(12) United States Patent
Yu et al.

(10) Patent No.: US 10,058,849 B2
(45) Date of Patent: Aug. 28, 2018

(54) METAL COMPLEX CATALYST, PREPARATION METHOD THEREOF, AND USE THEREOF IN PREPARING D,L-MENTHOL

(71) Applicants: ZHEJIANG NHU COMPANY LTD., Shaoxing, Zhejiang Province (CN); ZHEJIANG UNIVERSITY, Hangzhou, Zhejiang Province (CN); SHANDONG NHU PHARMACEUTICAL CO., LTD., Weifang, Shangdong Province (CN)

(72) Inventors: Ming Yu, Shaoxing (CN); Jintao Yuan, Shaoxing (CN); Haidong Yu, Shaoxing (CN); Weikang Shao, Shaoxing (CN); Yuhong Zhang, Hangzhou (CN)

(73) Assignees: ZHEJIANG NHU COMPANY LTD., Shaoxing (CN); ZHEJIANG UNIVERSITY, Hangzhou (CN); SHANDONG NHU PHARMACEUTICAL CO., LTD., Weifang (CN)

( * ) Notice: Subject to any disclaimer, the term of this patent is extended or adjusted under 35 U.S.C. 154(b) by 0 days.

(21) Appl. No.: 15/565,593

(22) PCT Filed: May 10, 2016

(86) PCT No.: PCT/CN2016/081518
§ 371 (c)(1),
(2) Date: Oct. 10, 2017

(87) PCT Pub. No.: WO2016/184328
PCT Pub. Date: Nov. 24, 2016

(65) Prior Publication Data
US 2018/0111113 A1  Apr. 26, 2018

(30) Foreign Application Priority Data

May 21, 2015 (CN) .......................... 2015 1 0264486

(51) Int. Cl.
*B01J 23/847* (2006.01)
*C07C 35/12* (2006.01)
*C07C 29/20* (2006.01)
*C07C 29/56* (2006.01)

(52) U.S. Cl.
CPC .......... *B01J 23/8472* (2013.01); *C07C 29/20* (2013.01); *C07C 29/56* (2013.01); *C07C 35/12* (2013.01); *B01J 2523/31* (2013.01); *B01J 2523/55* (2013.01); *B01J 2523/845* (2013.01); *B01J 2523/847* (2013.01); *C07C 2601/14* (2017.05)

(58) Field of Classification Search
CPC ............. B01J 23/8472; B01J 2523/847; B01J 2523/845; B01J 2523/55; B01J 2523/31; C07C 29/20; C07C 29/56; C07C 2601/14
See application file for complete search history.

(56) References Cited

U.S. PATENT DOCUMENTS 4,134,919 A  1/1979 Yamanaka et al.

FOREIGN PATENT DOCUMENTS

| CN | 103058825 A | * | 4/2013 | ............. B01J 25/02 |
| CN | 103058825 A | | 4/2013 | |

* cited by examiner

*Primary Examiner* — Rosalynd A Keys
(74) *Attorney, Agent, or Firm* — Jiwen Chen

(57) ABSTRACT

The present invention discloses a metal complex catalyst, its preparing method and its application in preparing D,L-menthol, the metal complex catalyst includes weight percent elements as follows: 70-85% of Ni, 8-10% of Al, 5-10% of V, and 2-10% of Co. When this metal complex catalyst is applied in preparing D,L-menthol through thymol hydrogenation, it has the characteristics of high reaction activity and quick racemization of chiral compound. Meanwhile, a certain kind of alkali added in isomerization is the key to reducing light constituent byproduct. The whole process comes in good reaction selectivity, simple preparing technology, low production cost, and environment-friendly synthetic route.

10 Claims, No Drawings

METAL COMPLEX CATALYST, PREPARATION METHOD THEREOF, AND USE THEREOF IN PREPARING D,L-MENTHOL

This is a U.S. national stage application of PCT Application No. PCT/CN2016/081518 under 35 U.S.C. 371, filed May 10, 2016 in Chinese, claiming priority of Chinese Application No. 201510264486.4, filed May 21, 2015, all of which are hereby incorporated by reference.

TECHNICAL FIELD

The present invention belongs to organic synthesis technical field, specifically relates to a method for synthesizing D,L-menthol, and a method for isomerically synthesizing D,L-menthol for other seven isomers of L-menthol (including D-menthol, D,L-neomenthol, D,L-isomenthol, and D,L-neoisomenthol).

BACKGROUND ART

L-menthol, which has the structure as shown in formula (I), is in wide application thanks to its unique cool and refreshing effect. Currently, its global consumption amount is about 40 thousand tons annually, playing an important role in the flavor industry. There are two ways for obtaining L-menthol: natural extraction and chemical synthesis. Currently, natural extraction is still the dominant way of production, accounting for about 80% of the market share. The rest of 20% or so is made through chemical synthesis, comprising racemized menthol splitting synthesis method and asymmetric synthesis method. Currently, due to being subject to the limit of chiral catalyst and transition metal catalyst, asymmetric synthesis method is applied by a few companies only. Although the method of synthesizing L-menthol from racemized menthol is simple, one problem of the method is that D-menthol (II) at amount equivalent to L-menthol is produced. However, currently, the market capacity for D-menthol is very less. Presently, the solution is generally like this: translating D-menthol into racemized menthol first, then splitting to obtain L-menthol, repeating such process until it is fully translated into L-menthol. Besides, the most common method for synthesizing racemized menthol is from thymol hydrogenation. However, based on the current technical methods, it's very difficult to control the reaction to produce racemized menthol only, high proportion of product has resulted in other three pairs of isomers. Therefore, in this method of synthesizing L-menthol, how to efficiently translate D-menthol and other three pairs of isomers into racemized menthol is the critical factor for obtaining L-menthol at high yield.

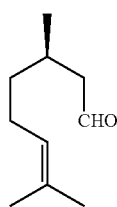

(I)

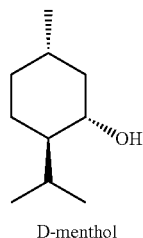

D-menthol (II)

Introduced below are a few reported methods for translating D-menthol and other three pairs of isomers into racemized menthol:

DE 2314813A1 describes hydrogenation of thymol using a Co/Mn catalyst fixed bed at 170~220° C. temperature and 20 MPa pressure. The embodiments of that patent are implemented at 180~210° C. temperatures and over 20 MPa pressure, and a mixture of 8 kinds of menthol stereoisomers is produced, consisting of 56.5~59% of racemized menthol and 10.6~10.8% of racemized isomenthol. And 4~5% of light constituents exist in the mixture, which are non-recyclable by-products.

Bayer Corporation of Germany describes in U.S. Pat. No. 5,756,864 that: in fixed bed reaction, Ni, Mn and alkaline earth metal hydroxide or oxide without carrier were used as a catalyst to isomerize D-menthol under the condition of 200~250° C. temperature and 100~300 bar hydrogen pressure to obtain racemized menthol of 59.8%, the catalyst used in the reaction remains highly active 6000 hours after the reaction.

Patent Application WO 2012/010695A1 describes the method that adopts γ-$Al_2O_3$ carrier-loaded Ru catalyst and rare earth catalyst containing alkali metal to translate menthol for rearrangement isomerization, the method can obtain D,L-menthol of 68% under the reaction condition of 90~120° C. and 1~1.2 Mpa, and the ratio of D,L-menthol/D,L-isomenthol is 6~8.5.

Patent Publication CN 103143363 A invented Cu/Ni catalyst with aluminium oxide as a carrier, which can achieve menthol content of up to 62.8% after the diastereoisomer of the menthol is isomerized.

SUMMARY OF THE INVENTION

The present invention provides a metal complex catalyst, its preparing method and its application in preparing D,L-menthol. The metal complex catalyst can improve the D,L-menthol content in hydrogenation reaction.

A metal complex catalyst, comprising the following elements of weight percentages:

| | |
|---|---|
| Ni | 70-85% |
| Al | 8-10% |
| V | 5-10% |
| Co | 2-10%. |

In the present invention, through controlling the content of the specific elements in the metal complex catalyst, the catalysis efficiency of the catalyst is effectively improved, when it is used for preparing D,L-menthol, it has higher catalysis efficiency than conventional raney nickel.

The present invention further provides a method for preparing the metal complex catalyst, comprising the following steps:

(1) Treating Ni—Al alloy with dilute sodium hydroxide solution, then water-washing it until it is neutral;

The mass percent concentration of the dilute sodium hydroxide solution is 3~8%;

(2) Adding the Ni—Al alloy treated in Step (1) batch by batch into the concentrated sodium hydroxide solution for reaction, after the reaction is completed, keeping it static and then washing to obtain intermediate;

The mass percent concentration of the concentrated sodium hydroxide solution is 15~25%;

(3) Adding vanadium nitrate solution and cobalt nitrate solution to the intermediate obtained in Step (2) for replacement reaction, after the reaction is completed, the metal complex catalyst can be obtained through post-treatment.

In the present invention, the Ni—Al alloy is sequentially treated by sodium hydroxides of different concentrations, not only the content of Ni and Al in alloy can be adjusted, but also the form shape of the intermediate can be adjusted. Finally, Al goes through replacement reaction with vanadium nitrate solution and cobalt nitrate solution to obtain metal complex containing four metals, namely Ni, Al, V and Co.

After the Ni—Al alloy goes through treatment by sodium hydroxide, wherein the content of Ni will increase and that of Al will decrease, the initial contents of Ni and Al in the Ni—Al alloy will affect the contents of the constituents in the final product, hence affecting the catalytic activity of the metal complex catalyst. As preferred selection, in Step (1), the weight percent content of Ni in the Ni—Al alloy is 50%~60%, that of Al is 40%~50%.

As preferred selection, in Step (1), the mass percent concentration of the dilute sodium hydroxide solution is 5%; the treatment temperature is 20~25° C., and the treatment duration is 1~3 hours.

As preferred selection, in Step (2), the concentration of the concentrated sodium hydroxide solution is 20%; the reaction temperature is 10~25° C., and the reaction duration is 8~12 hours.

The concentrations of vanadium nitrate and cobalt nitrate can also affect the constituents of the metal complex catalyst, hence affecting the catalytic efficiency of the catalyst. As preferred selection, in Step (3), the concentration of vanadium nitrate is 1~2 mol/L, and that of cobalt nitrate is 0.5~1 mol/L;

The molar ratio of vanadium nitrate to the Ni in the Ni—Al alloy is 1:8~15;

The molar ratio of cobalt nitrate to the Ni in the Ni—Al alloy is 1:30~40.

The present invention further provides a method for preparing D,L-menthol, comprising the following steps:

(1) Under the effect of the metal complex catalyst and hydrogen, thymol goes through a hydrogenation reaction, the produced hydrogenation product is rectified to obtain the D,L-menthol and residual fraction;

(2) Under the effect of the metal complex catalyst and hydrogen, the residual fraction obtained in Step (1) further goes through isomerization reaction, the produced isomerization product is rectified to obtain D,L-menthol.

The D,L-menthol in the present invention refers to racemized menthol, containing D-menthol and L-menthol.

Test results show that when the catalyst obtained from the preparing method of the present invention is applied in preparing D,L-menthol, higher catalytic efficiency is achieved, and the D,L-menthol proportion in the product can be improved.

In Step (1), the pressure of hydrogenation reaction is 2~8 Mpa, and the temperature of that is 120~220° C.

In Step (1), the hydrogenation reaction is conducted under pH8~10 alkaline condition, the alkali to be used is alkali metal or alkaline earth metal hydroxide. Specifically, it is one of sodium hydroxide, potassium hydroxide, barium hydroxide, calcium hydroxide, potassium carbonate and calcium carbonate or combination of two of them. If combination is adopted, generally, the two kinds of alkalis to be added are at the same weight.

In Step (1), the hydrogenation reaction is conducted in a nonpolar solvent, e.g., various lower paraffin solvents, including normal hexane, cyclohexane, n-pentane, preferred selection is cyclohexane.

In Step (1), D,L-menthol at content over 99% can be obtained from rectification of the hydrogenated product, meanwhile, residual fraction containing DL-menthol of 3~5% weight is also obtained.

In Step (2), the pressure of isomerization reaction is 2~3 Mpa, and the temperature of that is 80~120° C.

In Step (2), the materials of the isomerization reaction include various isomers of menthol (including neomenthol, neoisomenthol, isomenthol and menthol) or their mixture.

In Step (2), the solvents of the isomerization reaction are non-polar solvents, including: one of normal hexane, cyclohexane and petroleum ether, preferred selection is cyclohexane.

In Steps (1) and (2), preferred weight ratio of the metal complex catalyst to material is 1:10~30.

In Step (2), adding catalytic amount of alkali can help to reduce the isomerization reaction is conducted under the catalysis of alkaline, and the weight ratio of alkaline to material is 1:10~30. As preferred selection, the alkali is alkali metal or alkaline earth metal hydroxide. Specifically, it is one of sodium hydroxide, potassium hydroxide, barium hydroxide, calcium hydroxide, potassium carbonate and calcium carbonate or combination of two of them. If the combination is adopted, the two kinds of alkalis to be added are generally at the same weight.

In Step (2), the product obtained from isomerization reaction contains D,L-menthol at about 60~70% weight, D,L-isomenthol at about 7~9% weight, neomenthol at about 20~25% weight, and neoisomenthol at about 1~5% weight. D,L-menthol at content up to 99% or above can be obtained through distillation.

The solvent of the hydrogenation reaction in Step (1) can be the same as that of the isomerization reaction in Step (2).

The present invention further provides another method for preparing D,L-menthol, comprising the following steps:

Under the effect of the metal complex catalyst and hydrogen, the material containing menthol isomer goes through isomerization reaction, the produced isomerization product is rectified to obtain D,L-menthol.

Wherein the mixture left after D,L-menthol is rectified and separated from the mixture of isomers, or D-menthol from splitting L-menthol or purchased natural menthol can be used as material containing menthol isomer. Its constituents comprise: L-menthol, D-menthol, D,L-isomenthol, D,L-neomenthol, D,L-neoisomenthol or mixture of these isomers. L-menthol is natural menthol, D-menthol generally contains 5~7% of L-menthol, other materials generally contains 3~6% of D,L-menthol.

The solvents of the isomerization reaction are non-polar solvents, including: one of normal hexane, cyclohexane and petroleum ether.

The beneficial effects of the present invention: through preferred combination of several metal elements, improve the D,L-menthol content in isomerization reaction, achieving higher reaction activity, and the adding of catalytic amount of alkali reduces production of non-usable paraffin by-product.

SPECIFIC EMBODIMENTS OF THE PRESENT INVENTION

Embodiment 1: Preparing Metal Complex Catalyst A

The metal complex catalyst A in this embodiment comprises 85% of Ni, 8% of Al, 5% of V, and 2% of Co (weight percentage). The synthesizing steps are as follows:

(1) At 25° C., Ni—Al alloy was treated with sodium hydroxide solution at mass percent concentration of 5% (in the alloy, the weight percent content of Ni is 56%, that of Al is 44%) for 2 hours, water-wash until it was neutral, at this stage, the contents of Ni—Al alloy had no obvious change.

(2) In 4 L beaker, 380 g sodium hydroxide was dissolved in 1.5 L distilled water, stirred, cooled on ice bath to 10° C. While stirring, 300 g Ni—Al alloy treated in Step (1) was added batch by batch in a small amount into the alkali liquor, the adding speed was controlled not to allow the solution temperature to exceed 25° C. (on ice bath). After it was fully added (it took about 2 hours), stirring was stopped, the beaker was taken away from the ice bath, the reaction solution was allowed to rise to room temperature. When the hydrogen generation was slow, the reaction solution was heated slowly on the boiling water bath (no fast temperature rise, otherwise there can be too many bubbles, and the reaction solution may spill), until the bubble generation slowed down again (about 8~12 hours, during this time, the volume of the solution was maintained basically constant by replenishing distilled water). Then it was kept static to allow the Ni powder to settle down, and the supernatant was poured out. Distilled water was added until it reached the original volume, the solution was stirred to allow the Ni powder to suspend, kept static again to allow the Ni powder to settle down, the supernatant was poured out. Then the Ni power was transfer to 2 L beaker, the supernatant was removed, 500 ml water solution containing 50 g sodium hydroxide was added, stirred, kept static, the supernatant was poured out. 500 ml distilled water was added again, stirred, kept static, the supernatant was poured out. It as water-washed in this way for several times until the eluate shows neutrality against the litmus paper, then water-washed for 10 more times (water-wash for about 20~40 times). The supernatant was poured out, poured in 100 mL vanadium nitrate (2N) and cobalt nitrate (0.8N) solutions and stirred for 4 hours, the catalyst was allowed to settle down, the supernatant was poured out. 200 mL 95% ethanol was added, washed using decantation method for three times, and washed again using waterless ethanol for three times. The obtained metal complex catalyst was stored in grinding jar filled with waterless ethanol (no contact with air), the catalyst must be kept under the liquid surface, the metal complex catalyst A suspending in the liquid weighs about 150 g. Based on XPS analysis, the product contains 85% of Ni, 8% of Al, 5% of V, and 2% of Co.

Embodiment 2 Preparing Metal Complex Catalyst B

The metal complex catalyst B in this embodiment comprises 75% of Ni, 10% of Al, 10% of V, and 5% of Co (weight percentage). The synthesizing steps are as follows:

(1) At 25° C., Ni—Al alloy was treated with sodium hydroxide solution at mass percent concentration of 5% (in the alloy, the weight percent content of Ni is 50%, that of Al is 50%), allowed to react for 2 hours, water-wash until it was neutral.

(2) In 4 L beaker, 380 g sodium hydroxide was dissolved in 1.5 L distilled water, stirred, cooled on ice bath to 10° C. While stirring, 300 g Ni—Al alloy treated in Step (1) was added batch by batch in a small amount into the alkali liquor, the adding speed was controlled not to allow the solution temperature to exceed 25° C. (on ice bath). After it was fully added (it took about 2 hours), stopped stirring, the beaker was taken away from the ice bath, the reaction solution was allowed to rise to room temperature. If the hydrogen generation is slow, the reaction solution was heated slowly on the boiling water bath (no fast temperature rise, otherwise there can be too many bubbles, and the reaction solution may spill), until the bubble generation slows down again (about 8~12 hours, during this time, the volume of the solution was maintained basically constant by replenishing distilled water). Then it was kept static to allow the Ni powder to settle down, and poured out the supernatant. Distilled water was added until it reached the original volume, the solution was stirred to allow the Ni powder to suspend, kept static again to allow the Ni powder to settle down, the supernatant was poured out. Then settled Ni powder was transferred to 2 L beaker, the supernatant was removed, 500 ml water solution containing 50 g sodium hydroxide was added, stirred, kept static, the supernatant was poured out. 500 ml distilled water was added again, stirred, kept static, the supernatant was poured out. It was water-washed in this way for several times until the eluate shows neutrality against the litmus paper, then it was water-washed for 10 more times (water-wash for about 20~40 times). Supernatant was poured out, poured in 200 mL vanadium nitrate (2N) and cobalt nitrate (0.8N) solutions and stirred for 4 hours, allowed the catalyst to settle down, the supernatant was poured out. 200 mL 95% ethanol was added, washed using decantation method for three times, and washed again using waterless ethanol for three times. The obtained metal complex catalyst was stored in grinding jar filled with waterless ethanol (no contact with air), the catalyst must be kept under the liquid surface, the metal complex catalyst B suspending in the liquid weighs about 144 g. Based on XPS analysis, the product contains 75% of Ni, 10% of Al, 10% of V, and 5% of Co.

Embodiment 3 Preparing Metal Complex Catalyst C

The metal complex catalyst C in this embodiment comprises consists of 80% of Ni, 8% of Al, 7% of V, and 5% of Co (weight percentage). The synthesizing steps are as follows:

(1) At 25° C., Ni—Al alloy was treated with sodium hydroxide solution at mass percent concentration of 5% (in the alloy, the weight percent content of Ni is 54%, that of Al is 46%), allowed to react for 2 hours, water-washed until it was neutral.

(2) In 4 L beaker, 380 g sodium hydroxide was dissolved in 1.5 L distilled water, stirred, cooled on ice bath to 10° C. While stirring, 300 g Ni—Al alloy treated in Step (1) was added batch by batch in a small amount into the alkali liquor, the adding speed was controlled not to allow the solution temperature to exceed 25° C. (on ice bath). After it was fully added (it took about 2 hours), stirring was stopped, the beaker was taken away from the ice bath, the reaction solution was allowed to rise to room temperature. If the hydrogen generation was slow, the reaction solution was heated slowly on the boiling water bath (no fast temperature rise, otherwise there can be too many bubbles, and the reaction solution may spill), until the bubble generation slowed down again (about 8~12 hours, during this time, the volume of the solution was maintained basically constant by replenishing distilled water). Then it was kept static to allow the Ni powder to settle down, and the supernatant was poured out. Distilled water was added until it reached the original volume, the solution was stirred to allow the Ni powder to suspend, kept static again to allow the Ni powder to settle down, the supernatant was poured out. Then transfer to 2 L beaker, the supernatant was removed, add 500 ml water solution containing 50 g sodium hydroxide, stirred, kept static, the supernatant was poured out. 500 ml distilled water was added again, stirred, kept static, the supernatant was poured out. It was water-washed in this way for several times until the eluate showed neutrality against the litmus paper, then it was water-washed for 10 more times (water-wash for about 20~40 times). Supernatant was poured out, poured in 150 mL vanadium nitrate (2N) and cobalt nitrate (0.8N) solutions and stirred for 4 hours, allowed the catalyst to settle down, the supernatant was poured out. 200 mL 95% ethanol was added, washed using decantation method for three times, and washed again using waterless ethanol for three times. The obtained metal complex catalyst was stored in grinding jar filled with waterless ethanol (no contact with air), the catalyst must be kept under the liquid surface, the metal complex catalyst C suspending in the liquid weighs about 146 g. Based on XPS analysis, the product contains 80% of Ni, 8% of Al, 7% of V, and 5% of Co.

repeating charging and discharging nitrogen for 3 times again, basically empty the nitrogen in the autoclave, then introducing hydrogen to allow the pressure in the autoclave to reach 4 MPa.

(4) Start reaction: the temperature was set to 150° C. allow autoclave to raise temperature slowly, started stirring and circulating cooling water at stirring speed of 500 r/min, when the temperature reached 180° C., adjusting the set temperature to 180° C., and raised the hydrogen pressure to 6.0 MPa. After two hours, it was sampled to test the condition of isomers to allow the contents of the isomers to reach balance, recorded the mass percent contents of the isomers, the results were as shown in Table 1.

(5) Press material: after the reaction was completed, the reaction mixture was pressed out, filtered and removed catalyst, the used catalyst was sealed and stored in cyclohexane solvent for next time recycled use. The autoclave was washed to get ready for next time reaction.

(6) Remove cyclohexane: cyclohexane solvent was removed by rotating and distilling the filtrate to obtain crude product of mixture of menthol isomers.

(7) Distillation: the crude product of mixture of menthol isomers was distilled to remove the resolved low-boiling-point substance (preceding fraction), high-boiling-point substance (bottoms) was removed, the finished product of a mixture of menthol isomers was obtained. D,L-menthol product and residual fraction (containing small amount of D,L-menthol, neomenthol, neoisomenthol and isomenthol) were obtained through rectification.

TABLE 1

Reaction conditions & results of embodiments 4~9

| | Fed material | | Reaction | Light | Light | Isomer content (%) | | | | |
|---|---|---|---|---|---|---|---|---|---|---|
| No. | Thymol (g) | Cyclohexane (ml) | time (h) | constituent by-product 1 | constituent by-product 2 | Neomenthol | Menthol | Neoisomenthol | Isomenthol | Thymol |
| 4 | 2 | 30 | 7 | 1.35 | 1.65 | 23.86 | 60.31 | 2.53 | 9.35 | — |
| 5[a] | 2 | 30 | 7 | 2.86 | 3.25 | 25.18 | 53.33 | 3.51 | 10.92 | — |
| 6 | 10 | 100 | 7 | — | — | 26.6 | 61.01 | 2.48 | 9.78 | — |
| 7 | 20 | 100 | 7 | — | — | 22.00 | 50.21 | 3.66 | 15.57 | — |
| | | | 12 | 1.36 | 1.53 | 23.99 | 60.39 | 2.44 | 8.96 | 0.70 |
| 8 | 30 | 100 | 5 | 0.61 | 0.84 | 17.75 | 48.88 | 3.33 | 6.80 | 21.02 |
| | | | 11.5 | 1.65 | 1.69 | 22.96 | 62.40 | 2.31 | 8.07 | 0.26 |
| 9 | 40 | 100 | 7.5 | 0.05 | 0.08 | 15.09 | 40.02 | 4.59 | 10.93 | 29.24 |
| | | | 11.5 | 0.07 | 0.12 | 18.43 | 64.45 | 4.66 | 11.91 | 0.36 |
| | | | 15.5 | 0.79 | 0.68 | 20.54 | 67.29 | 2.51 | 8.12 | 0.07 |

[a]Used market raney nickel as catalyst.

Embodiments 4~9 Thymol Hydrogenation Reaction

Operating steps were as follows:

(1) Preparation: an operator cleaned autoclave, tested pressure, checked air tightness. Modified metal complex catalyst A was washed with ethanol to dehydrate, then washed with cyclohexane to remove ethanol. The cyclohexane liquid was sealed for future use.

(2) Feed material: under the condition that the autoclave was in good air tightness, thymol, cyclohexane solvent and 1.5 g metal complex catalyst A washed already were added, 0.5N sodium hydroxide was added to adjust pH to 9.

(3) Replacement: Charging and discharging nitrogen were repeated for 3 times, basically empty the air in the autoclave, The results of Embodiments 4~9 show that when the metal complex catalyst of the present invention was used instead of raney nickel, the menthol content in the hydrogenation reaction is obviously improved.

Embodiments 10~11 Isomerization Reaction

Operating steps are as follows:

(1) Preparation: a use cleaned autoclave, tested pressure, checked air tightness. Modified metal complex catalyst A was washed with ethanol to dehydrate, then washed with cyclohexane to remove ethanol. The cyclohexane liquid was sealed for future use.

(2) Feed material: under the condition that the autoclave was in good air tightness, isomerization material, 100 ml cyclohexane solvent and 1.5 g metal complex catalyst A washed already were added, 0.5N sodium hydroxide was added to adjust pH to 9.

(3) Replacement: an operator repeated charging and discharging nitrogen for 3 times, basically empty the air in the autoclave, repeated charging and discharging nitrogen for 3 times again, basically empty the nitrogen in the autoclave, then introduced hydrogen to allow the pressure in the autoclave to reach 2 MPa.

(4) Start reaction: temperature was set to 80° C. allow autoclave to raise temperature slowly, an operator started stirring and circulating cooling water at stirring speed of 500 r/min, when the temperature reached 100° C., adjusted the set temperature to 100° C., and raised the hydrogen pressure to 3.0 MPa. After two hours, sample was taken to test the condition of isomers to allow the contents of the isomers to reach balance, recorded the mass percent contents of the isomers, the results are as shown in Table 2.

(5) Press material: after the reaction was completed, the reaction mixture was pressed out, filtered and catalyst was removed, the used catalyst was sealed and stored in cyclohexane solvent for next time recycled use. The autoclave was washed to get ready for next time reaction.

(6) Remove cyclohexane: cyclohexane solvent was removed by rotating and distilling the filtrate to obtain crude product of mixture of menthol isomers.

(7) Distillation: the crude product of mixture of menthol isomers was removed to remove the resolved low-boiling-point substance (preceding fraction), high-boiling-point substance (bottoms) was removed, finished product of mixture of menthol isomers was obtained.

| Ni | 70-85% |
|---|---|
| Al | 8-10% |
| V | 5-10% |
| Co | 2-10%. |

2. The method for preparing metal complex catalyst according to claim 1, comprising the following steps:
  (1) treating Ni—Al alloy with a dilute sodium hydroxide solution, then water-washing the treated Ni—Al alloy until neutral;
  the mass percent concentration of the dilute sodium hydroxide solution is 3~8%;
  (2) adding the Ni—Al alloy treated in Step (1) batch by batch into the concentrated sodium hydroxide solution for reaction, after the reaction being completed, keeping the reaction solution static and then washing to obtain intermediate;
  the mass percent concentration of the concentrated sodium hydroxide solution is 15~25%;
  (3) adding vanadium nitrate solution and cobalt nitrate solution to the intermediate obtained in Step (2) for replacement reaction, after the reaction being completed, the metal complex catalyst is obtained through post-treatment.

3. The method for preparing metal complex catalyst according to claim 2, wherein: in Step (1), the weight percent content of Ni in the Ni—Al alloy is 50%~60%, the weight percent content of Al is 40%~50%.

4. The method for preparing metal complex catalyst according to claim 2, wherein: in Step (1), the mass percent concentration of the dilute sodium hydroxide solution is 5%;

TABLE 2

Reaction conditions & results of embodiments 10~12

| No. | Material designation/ material feeding amount g | Menthol constituent | Isomer content (%) | | | | | | |
|---|---|---|---|---|---|---|---|---|---|
| | | | Light constituent 1 | Light constituent 2 | Neomenthol | Menthol | Neoisomenthol | Isomenthol | D/L-menthol |
| 10 | Menthol mixture A 10 g | Pre-reaction constituents contents | 0 | 0 | 6.83 | 20.41 | 2.75 | 70.01 | 10/10 |
| | | Post-reaction constituents contents | 0.13 | 0.41 | 20.85 | 68.74 | 2.60 | 7.27 | 34/34 |
| 11 | Menthol mixture B 10 g | Pre-reaction constituents contents | 0 | 0 | 83.76 | 8.29 | 7.83 | 0.12 | 4/4 |
| | | Post-reaction constituents contents | 0.24 | 0.38 | 24.18 | 67.88 | 2.11 | 5.21 | 32/32 |
| 12 | D-menthol 10 g | Pre-reaction constituents contents | 0 | 0 | 0.93 | 98.7 | 0.25 | 0.12 | 93/6 |
| | | Post-reaction constituents contents | 0.27 | 0.39 | 21.17 | 70.24 | 3.21 | 4.72 | 35/35 |

$^a$In Embodiments 10~12, the reaction time is 11 hours.

The results of Embodiments 10~12 show that when the metal complex catalyst of the present invention was used for the isomerization reaction of menthol, good results were also achieved.

The invention claimed is:

1. A metal complex catalyst comprising the following elements of weight percentages:

the treatment temperature is 20~25° C., and the treatment duration is 1~3 hours.

5. The method for preparing metal complex catalyst according to claim 2, wherein: in Step (2), the mass percent concentration of the concentrated sodium hydroxide solution is 20%; the reaction temperature is 10~25° C., and the reaction duration is 8~12 hours.

6. The method for preparing metal complex catalyst according to claim 2, wherein: in Step (3), the concentration of vanadium nitrate is 1~2 mol/L, that of cobalt nitrate is 0.5~1 mol/L;

the molar ratio of vanadium nitrate to the Ni in the Ni—Al alloy is 1:8~15; and the molar ratio of cobalt nitrate to the Ni in the Ni—Al alloy is 1:30~40.

7. A method for preparing D,L-menthol, comprising the following steps:
   (1) under the effect of the metal complex catalyst in claim 1 and hydrogen, thymol going through hydrogenation reaction, rectifying the produced hydrogenation product to obtain the D,L-menthol and residual fraction;
   (2) under the effect of the metal complex catalyst in claim 1 and hydrogen, the residual fraction obtained in Step (1) further going through isomerization reaction, rectifying the produced isomerization product to obtain D,L-menthol.

8. The method for preparing D,L-menthol according to claim 7, wherein: in Step (1), the pressure of hydrogenation reaction is 2~8 Mpa, and the temperature of that is 120~220° C.

9. The method for preparing D,L-menthol according to claim 7, wherein: in Step (2), the pressure of isomerization reaction is 2~3 Mpa, and the temperature of that is 80~120° C.;

the isomerization reaction is conducted under the catalysis of alkaline, and the weight ratio of alkaline to material is 1:10~30.

10. A method for preparing D,L-menthol, comprising the following steps:

under the effect of the metal complex catalyst in claim 1 and hydrogen, the material containing menthol isomer going through isomerization reaction, the produced isomerization product being rectified to obtain D,L-menthol.

* * * * *